United States Patent
Guillon et al.

(10) Patent No.: US 9,828,311 B2
(45) Date of Patent: Nov. 28, 2017

(54) METHOD FOR ISOMERIZING AN AROMATIC C8 FRACTION IN THE PRESENCE OF A CATALYST CONTAINING AN EUO ZEOLITE AND A SPECIFIC BINDER

(71) Applicant: IFP ENERGIES NOUVELLES, Rueil-Malmaison (FR)

(72) Inventors: Emmanuelle Guillon, Vourles (FR); Eric Sanchez, Saint Genis Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 143 days.

(21) Appl. No.: 14/366,006

(22) PCT Filed: Nov. 20, 2012

(86) PCT No.: PCT/FR2012/000474
§ 371 (c)(1),
(2) Date: Jun. 17, 2014

(87) PCT Pub. No.: WO2013/093222
PCT Pub. Date: Jun. 27, 2013

(65) Prior Publication Data
US 2014/0364668 A1    Dec. 11, 2014

(30) Foreign Application Priority Data

Dec. 20, 2011 (FR) ...................... 11 03995

(51) Int. Cl.
*C07C 5/27* (2006.01)
*B01J 29/74* (2006.01)
*B01J 29/22* (2006.01)
*B01J 35/10* (2006.01)

(52) U.S. Cl.
CPC .............. *C07C 5/2737* (2013.01); *B01J 29/22* (2013.01); *B01J 29/7446* (2013.01); *B01J 35/10* (2013.01); *B01J 35/1009* (2013.01); *B01J 35/1014* (2013.01); *B01J 35/1019* (2013.01); *C07C 5/2754* (2013.01); *B01J 35/1047* (2013.01); *B01J 35/1061* (2013.01); *B01J 2229/42* (2013.01); *C07C 2521/02* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2521/18* (2013.01); *C07C 2523/08* (2013.01); *C07C 2523/14* (2013.01); *C07C 2523/36* (2013.01); *C07C 2523/42* (2013.01); *C07C 2523/44* (2013.01); *C07C 2523/46* (2013.01); *C07C 2523/745* (2013.01); *C07C 2523/75* (2013.01); *C07C 2523/755* (2013.01); *C07C 2527/167* (2013.01); *C07C 2529/18* (2013.01); *C07C 2529/70* (2013.01); *C07C 2529/89* (2013.01); *C07C 2601/16* (2017.05); *Y02P 20/52* (2015.11)

(58) Field of Classification Search
CPC ........ B01J 29/22; B01J 35/10; B01J 35/1009; B01J 35/1014; B01J 35/1019; B01J 29/7446; C07C 5/2754; C07C 5/2737; C07C 15/08
USPC .......................................... 585/481; 423/714
See application file for complete search history.

(56) References Cited

U.S. PATENT DOCUMENTS

| | | | | |
|---|---|---|---|---|
| 4,762,957 A | * | 8/1988 | Sachtler | .................. B01J 29/44 585/481 |
| 6,057,486 A | * | 5/2000 | Merlen | ................ B01J 29/7246 502/64 |
| 6,143,941 A | * | 11/2000 | Sharma | ................. C07C 5/2724 585/481 |
| 6,337,427 B1 | | 1/2002 | Alario et al. | |
| 7,525,008 B2 | | 4/2009 | Bogdan et al. | |
| 7,893,309 B2 | | 2/2011 | Guillon et al. | |
| 8,183,172 B2 | | 5/2012 | Guillon et al. | |
| 2005/0277796 A1 | | 12/2005 | Bogdan et al. | |
| 2008/0275281 A1 | | 11/2008 | Guillon et al. | |
| 2009/0299115 A1 | | 12/2009 | Guillon et al. | |
| 2011/0077146 A1 | * | 3/2011 | Whitchurch | ........... B01J 29/068 585/481 |

FOREIGN PATENT DOCUMENTS

| | | |
|---|---|---|
| EP | 0949229 A1 | 10/1999 |
| EP | 1985600 A1 | 10/2008 |
| WO | 2005065380 A2 | 7/2005 |
| WO | 2007080238 A1 | 7/2007 |

OTHER PUBLICATIONS

International Search Report from PCT/FR2012/000474 dated Apr. 25, 2013.

* cited by examiner

*Primary Examiner* — Brian McCaig
*Assistant Examiner* — Jason Chong
(74) *Attorney, Agent, or Firm* — Millen White Zelano and Branigan, PC; John Sopp; Csaba Henter

(57) ABSTRACT

A process for isomerizing an aromatic cut containing at least one aromatic compound containing eight carbon atoms per molecule is described, comprising bringing said cut into contact with at least one catalyst comprising at least one metal from group VIII of the periodic classification of the elements, at least one zeolitic support comprising a zeolite selected from zeolites with structure type EUO and MOR, used alone or as a mixture, and at least one matrix, such that the specific surface area of the matrix in the zeolitic support of said catalyst is in the range 5 to 200 m$^2$/g.

10 Claims, No Drawings

METHOD FOR ISOMERIZING AN AROMATIC C8 FRACTION IN THE PRESENCE OF A CATALYST CONTAINING AN EUO ZEOLITE AND A SPECIFIC BINDER

FIELD OF THE INVENTION

The present invention relates to the isomerization of an aromatic cut containing at least one aromatic compound containing eight carbon atoms per molecule with a view to the production of xylenes, in particular para-xylene. More particularly, the present invention relates to a process for the isomerization of an aromatic feed comprising at least one aromatic compound containing eight carbon atoms per molecule with a view to maximizing the production of para-xylene, said isomerization process employing a catalyst comprising at least one metal from group VIII supported on a particular zeolitic support. The present invention also relates to a process for the preparation of said catalyst.

PRIOR ART

Catalytic formulations for isomerizing xylenes which are known by the person of the art are generally based on a zeolite and a metal from group VIII shaped with a binder, usually an alumina binder. Zeolites used for the isomerization of aromatic C8 cuts include ZSM-5, used alone or as a mixture with other zeolites such as mordenite, for example. Those catalysts have been described in particular in patents U.S. Pat. Nos. 4,467,129, 4,482,773 and EP-B-0 013 617. Other catalysts, principally based on mordenite, have been described, for example, in patents U.S. Pat. Nos. 4,723,051, 4,665,258 and FR-A-2 477 903. More recently, a catalyst based on a zeolite with structure type EUO has been proposed (EP-A1-923 987). Patent application WO-A-2005/065380 describes the use of a zeolite with structure type MTW for the isomerization of xylenes and ethylbenzene. Application WO2010/000652 describes the use of a catalyst constituted by ZSM-12 zeolite and an alumina binder, with a pore volume of more than 0.6 $m^3/g$ and a specific surface area of more than 250 $m^2/g$.

SUBJECT MATTER AND ADVANTAGE OF THE INVENTION

The present invention concerns a process for isomerizing an aromatic cut containing at least one aromatic compound containing eight carbon atoms per molecule, comprising bringing said cut into contact with at least one catalyst comprising at least one metal from group VIII of the periodic classification of the elements, at least one zeolitic support comprising a zeolite selected from zeolites with structure type EUO and MOR, used alone or as a mixture, and at least one matrix, such that the specific surface area of the matrix in the zeolitic support of said catalyst is in the range 5 to 200 $m^2/g$.

It has surprisingly been discovered that a catalyst in the form of extrudates, beads or trilobes comprising at least one metal from group VIII of the periodic classification of the elements, at least one zeolitic support comprising a zeolite selected from zeolites with structure type EUO and MOR, used alone or as a mixture, and at least one matrix, such that the specific surface area of the matrix in the zeolitic support of said catalyst is in the range 5 to 200 $m^2/g$, leads to improved catalytic performances in terms of activity when it is used in a process for the isomerization of an aromatic cut comprising at least one aromatic compound containing eight carbon atoms per molecule. In particular, such a catalyst is more active as regards the desired products, namely xylenes, and in particular para-xylene, than a catalyst of the prior art.

DESCRIPTION OF THE INVENTION

Summary of the Invention

The present invention concerns a process for isomerizing an aromatic cut containing at least one aromatic compound containing eight carbon atoms per molecule, comprising bringing said cut into contact with at least one catalyst comprising at least one metal from group VIII of the periodic classification of the elements, at least one zeolitic support comprising a zeolite selected from zeolites with structure type EUO and MOR, used alone or as a mixture, and at least one matrix, such that the specific surface area of the matrix in the zeolitic support of said catalyst is in the range 5 to 200 $m^2/g$.

Preferably, in accordance with the invention, the specific surface area of the matrix in the zeolitic support of said catalyst is in the range 20 to 160 $m^2/g$, more preferably in the range 50 to 160 $m^2/g$.

The catalyst of the invention advantageously comprises 1% to 90% by weight of zeolite with structure type EUO and/or MOR with respect to the total catalyst weight. According to the invention, the zeolite with structure type EUO is selected from EU-1, TPZ-3 and ZSM-50 zeolites or a mixture thereof; preferably, the zeolite with structure type EUO is EU-1 zeolite. In accordance with the invention, the zeolite with structure type MOR is mordenite. Advantageously, the zeolite used in the zeolitic support of the catalyst is a mixture of EU-1 zeolite and mordenite.

The catalyst of the invention advantageously comprises a quantity of metal(s) from group VIII in the range 0.01% to 4% by weight with respect to the total catalyst weight.

In a variation of the invention, said catalyst further comprises at least one metal selected from metals from groups IIIA, IVA and VIIB, said metal(s) being in a quantity of 2% by weight or less with respect to the total catalyst weight.

The present invention also concerns a process for the preparation of a catalyst in accordance with the invention, comprising at least the following steps:

i) synthesizing at least one zeolite with structure type EUO and/or MOR;
ii) preparing a zeolitic support by shaping said zeolite with at least one matrix;
iii) depositing at least one metal from group VIII of the periodic classification of the elements onto the zeolitic support obtained from the shaping step ii).

In accordance with the process of the invention, the zeolite synthesis step i) is advantageously followed by at least one step for calcining and at least one ion exchange step carried out before the shaping step ii).

In accordance with the process of the invention, the shaping step ii) is followed by a drying step carried out at a temperature in the range 100° C. to 150° C. for a period in the range 5 to 20 hours in an oven, then by a calcining step carried out at a temperature in the range 250° C. to 750° C. for a period in the range 1 to 8 hours.

The process for isomerizing a feed in accordance with the invention, in particular an aromatic cut containing at least one aromatic compound containing eight carbon atoms per molecule, is advantageously carried out with the catalyst of the invention at a temperature of 300° C. to 500° C., a partial pressure of hydrogen of 0.3 to 1.5 MPa, a total pressure of 0.45 to 1.9 MPa and an hourly space velocity, expressed in kilograms of feed introduced per kilogram of catalyst per hour, of 0.25 to 30 $h^{-1}$.

DETAILED DESCRIPTION OF THE INVENTION

The present invention concerns a process for isomerizing an aromatic cut containing at least one aromatic compound containing eight carbon atoms per molecule, comprising bringing said cut into contact with at least one catalyst comprising at least one metal from group VIII of the periodic classification of the elements, at least one zeolitic support comprising a zeolite selected from zeolites with structure type EUO and MOR, used alone or as a mixture, and at least one matrix, such that the specific surface area of the matrix in the zeolitic support of said catalyst is in the range 5 to 200 $m^2/g$.

In a variation of the process of the invention, the specific surface area of the matrix in said zeolitic support of the catalyst is in the range 5 to 200 $m^2/g$, preferably in the range 20 to 160 $m^2/g$, more preferably in the range 50 to 160 $m^2/g$, and still more preferably in the range 50 to 150 $m^2/g$.

In accordance with the invention, the zeolite used in the zeolitic support for the catalyst employed in the process of the invention is selected from zeolites with structure type EUO and MOR, used alone or as a mixture. Preferably, the zeolite with structure type EUO is selected from EU-1, TPZ-3 and ZSM-50 zeolites, used alone or as a mixture; more preferably, the zeolite with structure type EUO is EU-1 zeolite. In accordance with the invention, the zeolite with structure type MOR is mordenite. In a variation of the invention, the zeolite used in the zeolitic support for the catalyst is a mixture of EU-1 zeolite and mordenite.

Advantageously, the catalyst of the invention comprises 1% to 90% by weight of zeolite with structure type EUO and/or MOR, preferably 3% to 80% and still more preferably 4% to 60% by weight of zeolite with structure type EUO and/or MOR with respect to the total catalyst weight.

The catalyst of the invention advantageously comprises a quantity of metal(s) from group VIII in the range 0.01% to 4% by weight, preferably 0.05% to 2.0% by weight with respect to the total catalyst weight.

In accordance with the invention, the total pore volume of the catalyst, measured by nitrogen adsorption, is in the range 0.5 $cm^3/g$ to 1.5 $cm^3/g$.

Preferably, the catalyst of the invention has a macropore volume of less than 0.1 $cm^3/g$, preferably less than 0.05 $cm^3/g$, the pore volume being defined as being the volume of pores with a size of more than 50 nm.

In accordance the invention, the mean diameter of the mesopores of the catalyst, measured using the BJH method (dVmeso/2), is more than 8 nm, preferably more than 10 nm, preferably more than 12 nm, the term "mesopores" meaning pores with a dimension in the range 2 to 50 nm.

The mean diameter of the macropores of the catalyst, measured using the BJH method (dVmacro/2), is more than 60, preferably in the range 70 to 200 nm, more preferably in the range 70 to 150 nm.

Characterization Techniques

The specific surface area is defined by the BET specific surface area, determined by nitrogen adsorption in accordance with ASTM standard D 3663-78 established on the basis of the BRUNAUER-EMMETT-TELLER method described in the periodical "The Journal of the American Society", 60, 309 (1938).

The pore distribution, measured by nitrogen adsorption, is determined using the Barrett-Joyner-Halenda (BJH) method. The nitrogen adsorption-desorption isotherm according to the BJH method is described in the periodical "The Journal of the American Society", 73, 373 (1951), written by E P Barrett, L G Joyner and P P Halenda. The term "nitrogen adsorption volume" means the volume measured for $P/P_0=0.99$, at which pressure it is accepted that the nitrogen has filled all of the pores. The "mean nitrogen desorption diameter" is defined as a diameter whereby all pores below that diameter constitute 50% of the pore volume (Vp) measured on the nitrogen desorption branch of the isotherm.

The present invention also concerns the process for preparing the catalyst of the invention. The catalyst is prepared using a process comprising at least the following steps:
  i) synthesizing at least one zeolite with structure type EUO and/or MOR;
  ii) preparing a zeolitic support by shaping said zeolite with at least one matrix;
  iii) depositing at least one metal from group VIII of the periodic classification of the elements onto the zeolitic support obtained from the shaping step ii).

Step i), Zeolite Synthesis

The zeolites used in accordance with the invention are crystalline solids which comprise silicon and at least one element T selected from the group formed by aluminium, iron, gallium and boron, preferably from the group formed by aluminium and boron, and more preferably aluminium; with an overall Si/T atomic ratio of more than 5. The zeolites used in the invention are preferably in the acid form, such that the ratio Na/T is less than 15%, preferably less than 10%, more preferably less than 5%.

The described zeolites with structure type EUO and/or MOR are well known in the art and their pore structure and topography have been defined in the "Atlas of Zeolite Framework Types", Ch. Baerlocher, W. M. Meier, D. H. Olson, $7^{th}$ edition, 2007). EUO type zeolites have a mono-dimensional network of medium pores (10MR) with side pockets containing 12 tetrahedral atoms (12MR). MOR type zeolites have a wide-pore mono-dimensional network (12 MR).

The mode of preparation of the various zeolites is also well known to the skilled person. In general, the methods for preparing such zeolites comprise mixing a source of silicon, a source of an element T such as aluminium, a source of an alkali metal and an organic nitrogen-containing compound, acting as a template, in an aqueous medium. EU-1 zeolite, described in European patent application EP-A-0 042 226, is prepared using either an alkylated derivative of a polymethylene α-ω diammonium or a degradation product of said derivative, or again precursors of said derivative, as the template. TPZ-3 zeolite, described in European patent application EP-A-0 051 318, is prepared using the same template family as that employed for the synthesis of EU-1 zeolite. In particular, the use of the compound 1,6-N,N,N,N',N',N'-hexamethylhexamethylenediammonium is described. ZSM-50 zeolite, described in documents EP 0 159 845 and U.S. Pat. No. 4,640,829, is prepared using the dibenzyldimethylammonium (DBDMA) derivative as the template.

In addition, in order to carry out said step i) for preparing the zeolite with structure type EUO of the invention, the skilled person will usefully make reference to one or other of the references cited above describing the preparation of such zeolites.

The synthesis of mordenite is described by Meier et al (Kristallogr 115 (1961)). Kim et al (Zeolites 11 (1991) 745) describe the synthesis of mordenite zeolite in the absence of an organic nitrogen-containing template, using a mixture of sodium hydroxide, sodium aluminate and silica.

In accordance with the invention, the specific surface area of the zeolite obtained from step i) is advantageously more than 250 m²/g, preferably more than 350 m²/g. Preferably, the zeolite obtained from step i) of the invention is entirely microporous.

Preferably, step i) for synthesizing the zeolite is followed by at least one calcining step and by at least one ion exchange step carried out before shaping step ii).

Step for calcining the zeolite obtained from step i).

Said step for calcining the zeolite obtained from said step i) in a stream of air is intended to eliminate the organic template present in the micropores of said zeolite, for example the cation $R_1R_2R_3—N^+—(CH_2)_n—N^+—R_4R_5R_6$, preferably 1,6 N,N,N,N',N',N'-hexamethylhexamethylene diammonium when the zeolite synthesized during said step i) is EU-1 zeolite. In accordance with the invention, the step for calcining the zeolite obtained from said step i) is advantageously carried out at a temperature in the range 150° C. to 600° C., preferably in the range 200° C. to 600° C., more preferably in the range 250° C. to 550° C., for a period in the range 1 to 48 hours, preferably for a period in the range 1 to 30 hours.

Step for ion exchange carried out on the calcined zeolite obtained from step i).

In accordance with the invention, after calcining the zeolite obtained from step i), the zeolite may also undergo at least one ion exchange step. The ion exchange(s) following said calcining in a stream of dry air can eliminate at least a portion, preferably practically all of the alkali cation, in particular sodium, which may be present in the cationic position in the zeolite in its as-synthesized form. In accordance with the invention, each ion exchange step is carried out at a temperature which is preferably in the range 20° C. to 150° C. for a period which is advantageously in the range 2 hours to 10 hours. In accordance with the invention, said ion exchange step is carried out using at least one $NH_4NO_3$ or ammonium acetate solution.

Step ii)—Preparation of a Zeolitic Support by Shaping the Synthesized Zeolite with at Least One Matrix The process for preparing the catalyst of the invention is continued by carrying out step ii) for shaping the zeolite with at least one matrix.

According to the invention, step ii) for shaping the zeolite is carried out on the zeolite synthesized in accordance with step i) which may or may not have undergone calcining and/or one or more ion exchanges. These two latter operations may be carried out after step ii) for shaping the zeolite.

Said step ii) for shaping said zeolite with structure type EUO and/or MOR of the invention is carried out using a matrix selected from clays, magnesia, aluminas, silicas, titanium oxide, boron oxide, zirconia, aluminium phosphates, titanium phosphates, zirconium phosphates, silica-aluminas and charcoal or a mixture of at least two of these compositions. Preferably, the matrix is an alumina.

More particularly, shaping in said step ii) consists of mixing the zeolite selected from structure types EUO and/or MOR in a moist matrix gel, preferably alumina. Said moist matrix gel is generally obtained by mixing at least one acid and a powdered matrix for a period required to obtain a properly homogeneous paste, then shaping into an item that can be used in a catalytic reactor.

A matrix powder is a mainly solid compound, preferably an oxide or hydrate. Preferably, a hydrate is used, more preferably an aluminium hydrate. The loss on ignition of this hydrate will preferably be more than 15%. The alumina powders selected in accordance with the invention include commercial aluminas, such as the TH, TM, Pural or Dispersal grades from Sasol.

Shaping may be carried out using shaping techniques which are known to the skilled person, such as, for example: extrusion, bowl granulation, spray drying or pelletization. As an example, said paste obtained thereby can be passed through a die to form extrudates, advantageously with a diameter in the range 0.4 to 4 mm. Shaping may also be carried out in the presence of various constituents of the catalyst and by extrusion of the mineral paste obtained, by pelletization, shaping into beads in a rotary bowl granulator or drum granulator, drop coagulation, oil-drop, oil-up, or any other known process for agglomerating a powder containing alumina and optionally other ingredients selected from those mentioned above.

The catalysts used in accordance with the invention are in the shape of spheres or extrudates. However, the catalyst is advantageously in the form of extrudates with a length in the range 4 to 9 mm, more particularly in the range 2 to 5 mm. They are cylindrical in shape (they may or may not be hollow), they may be twisted cylinders, multilobes (2, 3, 4 or 5 lobes, for example), or rings. The cylindrical shape is the preferred shape, but any other shape may be employed.

Further, these supports used in accordance with the present invention may have been treated, as is well known to the skilled person, with additives in order to facilitate shaping and/or to improve the final mechanical properties of the supports. Examples of additives that may in particular be cited are cellulose, carboxymethylcellulose, carboxyethylcellulose, tall oil, xanthan gums, surfactants, flocculating agents such as polyacrylamides, carbon black, starches, stearic acid, polyacrylic alcohol, polyvinyl alcohol, biopolymers, glucose, polyethylene glycols, etc.

Extrusion may be carried out using any conventional commercially available tool. The paste obtained from mixing is extruded through a die, for example by means of a piston or a single or double extrusion screw. This extrusion step may be carried out using any method which is known to the skilled person.

The characteristic porosity of the zeolitic supports of the invention, in particular the specific surface area, is partially adjusted during this step for shaping the particles of the support and any type of matrix known to the skilled person is suitable. Non-exhaustive examples of influential shaping parameters are the water content, the quantity of acid, and the mixing period. Water can be added or removed to adjust the viscosity of the paste to be extruded. This step may be carried out at any stage of the mixing step.

The quantity of acid added during mixing prior to shaping is less than 30%, preferably in the range 0.5% to 30%, more preferably in the range 0.5% to 20% by weight of the anhydrous mass of the zeolite and matrix, preferably alumina, engaged in the synthesis. Nitric acid is preferred.

Optionally, a base can be added in order to neutralize the paste when shaping following mixing in the presence of acid; an example is ammonia, in a quantity in the range 1% to 50% of the anhydrous mass of zeolite and matrix engaged, preferably alumina.

The mixing period is advantageously in the range 5 minutes to 120 minutes, preferably in the range 5 minutes to 90 minutes, more preferably in the range 5 to 60 minutes. The zeolite may be added at any time during mixing.

Trace impurities may be present in the matrix used in accordance with the invention, for example Na, Fe, Si, or sulphur. They are preferably present in limited quantities. In accordance with the invention, the traces of sulphur are less than 0.2% by weight, the traces of $Na_2O$ are less than 0.01% by weight, and the traces of $SiO_2$ and $Fe_2O_3$ are less than 0.02% by weight with respect to the total matrix mass.

Advantageously, the zeolite associated with the matrix, also termed the zeolitic support in the context of the present invention, is shaped into beads, extrudates or trilobes, advantageously into the form of extrudates or trilobes, more preferably into the form of trilobes.

In a variation of the process of the invention, an element such as tin, cerium or phosphorus may advantageously be introduced during shaping step ii), for example by co-mixing.

Advantageously, the catalyst of the invention comprises 1% to 90% by weight of zeolite with structure type EUO and/or MOR, preferably 3% to 80% and more preferably 4% to 60% by weight of zeolite with structure type EUO and/or MOR, with the matrix constituting the complement to 100%.

The specific surface area of the zeolitic support of the catalyst depends on the quantity of zeolite present in the zeolitic support. It is equal to the sum of the specific surface areas of the two constituents, matrix and zeolite, weighted according to their mass in the zeolitic support. The choice of matrix used in the invention is such that at the end of shaping step ii), the specific surface area of the matrix in the zeolitic support is in the range 5 to 200 $m^2/g$, preferably in the range 20 to 160 $m^2/g$, more preferably in the range 50 to 160 $m^2/g$, and still more preferably in the range 50 to 150 $m^2/g$. The BET specific surface area of the matrix is obtained by subtracting the specific surface area of the EUO and/or MOR type zeolite (included in the zeolitic support and weighted for the mass introduced) from the total specific surface area of the zeolitic support of the catalyst.

The specific surface area of the zeolitic support is measured at the end of the step for drying and calcining the zeolitic support following shaping step ii).

Drying and calcining after shaping step ii).

In the process of the invention, the shaping step ii) is advantageously followed by a drying step then by a calcining step. In this case, the drying step is advantageously carried out at a temperature in the range 100° C. to 150° C. for a period in the range 5 to 20 hours in an oven, and the calcining step is advantageously carried out at a temperature in the range 250° C. to 750° C. for a period in the range 1 to 8 hours. It may be advantageous to carry out this calcining step in the presence of steam.

Step iii), for Depositing at Least One Metal from Group VIII on the Zeolitic Support In accordance with the invention, the process for preparing the catalyst is continued by carrying out step iii), which consists of introducing at least one metal from group VIII of the periodic classification of the elements onto the zeolitic support prepared in step ii).

Advantageously, said metal from group VIII is selected from iron, cobalt, nickel, ruthenium, rhodium, palladium, osmium, iridium and platinum, preferably from the noble metals platinum, palladium, nickel, iridium and highly preferably from palladium and platinum, used alone or as a mixture. Still more preferably, said metal from group VIII is platinum.

Advantageously, the catalyst of the invention comprises a quantity of metal(s) from group VIII in the range 0.01% to 4% by weight, preferably in the range 0.05% to 2.0% by weight with respect to the total weight of catalyst.

In accordance with step iii), said metal(s) from group VIII can be deposited onto the zeolitic support using the dry impregnation technique, the excess impregnation technique or by ion exchange; preferably, step iii) is carried out by the dry impregnation technique or by ion exchange, and still more preferably by ion exchange. When several metals are introduced, these may be introduced either all in the same manner or using different techniques.

Any precursors of the group VIII metals are suitable for depositing one or more metal(s) from group VIII onto the zeolitic support. In particular, for any noble group VIII metal, it is possible to use ammonia compounds or compounds such as, for example, ammonium chloroplatinate, platinum dicarbonyl dichloride, hexahydroxyplatinic acid, palladium chloride or palladium nitrate. The platinum is advantageously introduced in the form of hexachloroplatinic acid. The noble group VIII metal is preferably introduced by impregnation using an aqueous or organic solution of one of the metallic compounds cited above. Examples of organic solvents which may be cited are paraffinic, naphthenic or aromatic hydrocarbons containing 6 to 12 carbon atoms per molecule, for example, and halogenated organic compounds containing 1 to 12 carbon atoms per molecule, for example. Examples which may be cited are n-heptane, methylcyclohexane, toluene and chloroform. It is also possible to use mixtures of solvents.

During step iii) for depositing the metal from group VIII onto the zeolitic support obtained from shaping step ii), controlling certain of the parameters employed, in particular the nature of the precursor of the group VIII metal(s) used and/or the impregnation technique, means that deposition of said metal(s) can be orientated mainly onto the matrix or onto the zeolite or statistically over the zeolite-matrix ensemble, namely the whole of the zeolitic support.

Thus, in order to introduce the group VIII metal(s), preferably platinum and/or palladium, mainly onto the matrix, it is possible to carry out an anion exchange with hexachloroplatinic acid and/or hexachloropalladic acid, in the presence of a competing agent, for example hydrochloric acid. This deposition is preferably followed by calcining, for example at a temperature in the range 350° C. to 550° C., and for a period in the range 1 to 4 hours. With such precursors, the group VIII metal(s) is/are deposited mainly onto the matrix and said metal(s) are properly dispersed and have good macroscopic distribution through the catalyst grain.

It is also possible to envisage depositing the group VIII metal(s), preferably platinum and/or palladium, by cationic exchange such that said metal(s) are deposited mainly onto the zeolite. Thus, in the case of platinum, the precursor may, for example, be selected from:

ammonium compounds such as tetrammine platinum (II) salts with formula $Pt(NH_3)_4X_2$, hexammine platinum (IV) salts with formula $Pt(NH_3)_6X_4$; halogenopentammine platinum (IV) salts with formula $(PtX(NH_3)_5)X_3$; N-tetrahalogenodiammine platinum salts with formula $PtX_4(NH_3)_2$; and halogenated compounds with formula $H(Pt(acac)_2X)$;

X being a halogen selected from the group formed by chlorine, fluorine, bromine and iodine, X preferably being chlorine, and "acac" representing the acetylacetonate group (with empirical formula $C_5H_7O_2$), a derivative of acetylacetone. With such precursors, the group VIII metal(s) is/are deposited mainly on the zeolite and said metal(s) have good dispersion and good macroscopic distribution through the catalyst grain.

According to the invention, step iii) for depositing the group VIII metal on the zeolitic support is preferably accomplished by carrying out ion exchange with hexachloroplatinic acid.

In another variation of the process of the invention, step iii) also comprises depositing at least one additional metal selected from metals from groups IIIA, IVA and VIIB. Said metal selected from metals from groups IIIA, IVA and VIIB is advantageously selected from gallium, indium, tin and rhenium, preferably from indium, tin and rhenium.

In such a case, the catalyst of the invention advantageously comprises said metal(s) in a quantity of 2% by weight or less with respect to the total catalyst weight. Preferably, said quantity is in the range 0.01% to 2%, preferably in the range 0.05% to 1.0% by weight with respect to the total catalyst weight.

In the case in which the catalyst used in the isomerization process of the invention also contains at least one additional metal selected from metals from groups IIIA, IVA and VIIB, any of the techniques for depositing such a metal which are known to the skilled person and any precursors of said metals may be suitable. It is possible to add the group VIII metal(s) and that (those) from groups IIIA, IVA and VIIB either separately or simultaneously in at least one unitary step. When at least one metal from groups IIIA, IVA and VIIB is added separately, it is preferably added after the metal from group VIII.

The additional metal selected from metals from groups IIIA, IVA and VIIB may be introduced via compounds such as chlorides, bromides or nitrates of metals from groups IIIA, IVA and VIIB, for example. As an example, in the case of indium, the nitrate or chloride is advantageously used and in the case of rhenium, perrhenic acid is advantageously used. In the case of tin, the tin chlorides $SnCl_2$ and $SnCl_4$ are preferred. The additional metal selected from metals from groups IIIA, IVA and VIIB may also be introduced in the form of at least one organic compound selected from the group constituted by complexes of said metal, in particular polyketone complexes of the metal, and hydrocarbyl metals such as metal alkyls, cycloalkyls, aryls, alkylaryls and arylalkyls. In this latter case, the metal is advantageously introduced using a solution of an organometallic compound of said metal in an organic solvent. It is also possible to use organohalogen compounds of the metal. Particular examples of organic metal compounds which may be cited are tetrabutyltin, in the case of tin, and triphenylindium in the case of indium.

In addition, intermediate treatments such as calcining and/or reduction, for example, may be applied between successive deposits of the various metals.

Preparation of the catalyst of the invention is advantageously terminated by calcining, preferably at a temperature in the range 250° C. to 600° C., for a period in the range 0.5 to 10 hours. Preferably, calcining is preceded by drying, for example oven drying, at a temperature in the range 25° C. to 250° C., preferably in the range 40° C. to 200° C. Said drying step is preferably carried out as the temperature is being raised to carry out said calcining. Prior ex situ reduction of the catalyst may be carried out in a stream of hydrogen, for example at a temperature of 450° C. to 600° C., for a period of 0.5 to 4 hours.

In accordance with the invention, it may be advantageous to calcine the catalyst again after reduction, in the presence of air and possibly in the presence of steam, as disclosed in patent applications FR 0 702 941 and FR 0 702 943.

Said metal(s) from group VIII is (are) advantageously deposited such that the dispersion of said metal(s), determined by chemisorption, is 50% to 100%, preferably 60% to 100%, more preferably 70% to 100%. Said metal(s) from group VIII is (are) also advantageously deposited so as to obtain good distribution of said metal(s) in the shaped catalyst. This distribution is characterized by its profile obtained using a Castaing microprobe. The ratio of concentrations of each element from group VIII in the core of the grain with respect to the edge of that same grain, defined as the distribution coefficient, is advantageously 0.6:1 to 1.34:1, preferably 0.7:1 to 1.3:1.

In the case in which the catalyst contains no sulphur, reduction of the metal in hydrogen is advantageously carried out in situ before injecting the feed.

In the case in which the catalyst used in the invention contains sulphur, the sulphur is introduced onto the shaped, calcined catalyst containing the metal or metals cited above, either in situ prior to the catalytic reaction, or ex situ. Any sulphurization is carried out after reduction. In the case of in situ sulphurization, if the catalyst has not already been reduced, reduction is carried out before sulphurization. In the case of ex situ sulphurization, reduction is carried out followed by sulphurization. The sulphurization is carried out in the presence of hydrogen using any sulphurizing agent which is well known to the skilled person, such as dimethyl sulphide or hydrogen sulphide, for example. As an example, the catalyst may be treated with a feed containing dimethyl sulphide in the presence of hydrogen, with a concentration such that the sulphur/metal atomic ratio is 1.5. The catalyst is then kept at approximately 400° C. in a flow of hydrogen for approximately 3 hours before injecting it into the feed. In the case in which the catalyst used in the invention contains sulphur, the quantity of sulphur in the catalyst is such that the ratio of the number of sulphur atoms to the number of metal atoms from group VIII which are deposited is up to 2:1, advantageously from 0.5:1 to 2:1.

Use of Catalyst of the Invention

The isomerization process of the invention consists of bringing an aromatic cut containing at least one aromatic compound containing eight carbon atoms per molecule into contact with at least said catalyst as described above in the present description.

In the process of the invention, said aromatic cut in particular comprises either solely a mixture of xylenes, or solely ethylbenzene, or a mixture of xylene(s) and ethylbenzene. Said isomerization process of the invention is generally carried out under the following operating conditions:
 a temperature of 300° C. to 500° C., preferably 320° C. to 450° C. and more preferably 340° C. to 430° C.;
 a partial pressure of hydrogen of 0.3 to 1.5 MPa, preferably 0.4 to 1.2 MPa and more preferably 0.7 to 1.2 MPa;
 a total pressure of 0.45 to 1.9 MPa, preferably 0.6 to 1.5 MPa; and
 an hourly space velocity, expressed as kilograms of feed introduced per kilogram of catalyst per hour, of 0.25 to 30 $h^{-1}$, preferably 1 to 10 $h^{-1}$ and more preferably 2 to 6 $h^{-1}$.

The following examples illustrate the invention without in any way limiting its scope.

EXAMPLE 1

Preparation of a EU-1 Zeolite

The starting material used was an as-synthesized EU-1 zeolite comprising the organic template, namely 1,6 N,N,N,N',N',N'-hexamethylhexamethylene diammonium, and with an overall Si/Al atomic ratio of 15.3 and a sodium content by weight corresponding to an Na/Al atomic ratio (%) of 30.8. This zeolite was synthesized in accordance with the disclosure in patent EP-B1-0 042 226. To prepare such a zeolite, the reaction mixture had the following molar composition:

60 SiO$_2$:10.6 Na$_2$O:5.27 NaBr:1.5 Al$_2$O$_3$:19.5 Hexa-Br$_2$:2777 H$_2$O.

Hexa-Br$_2$ is 1,6 N,N,N,N',N',N'-hexamethylhexamethylene diammonium, with the bromine as the counter-ion. The reaction mixture was placed in an autoclave, with stirring (300 rpm), for 5 days at 180° C.

This EU-1 zeolite initially was dry calcined at 550° C. in a stream of dry air for 24 hours in order to eliminate the organic template. Next, the solid obtained underwent four ion exchanges in a 10N NH$_4$NO$_3$ solution at approximately 100° C., taking 4 hours for each exchange. The solid obtained was given reference EU-1 (1) and had an overall Si/Al atomic ratio of 15.3 and a Na/Al atomic ratio of 0.51%.

The prepared EU-1 zeolite had a BET surface area of 410 m$^2$/g.

EXAMPLE 2 (Not in Accordance)

Preparation of Catalyst A Comprising a EU-1 Zeolite

The EU-1 (1) zeolite obtained in Example 1 was then shaped by extrusion with a commercial alumina gel (Pural SB3 from Sasol) so as to obtain, after drying at a temperature of 100° C. overnight and calcining in dry air carried out at a temperature of 450° C. for 4 hours, the support S1 which contained 8% by weight of EU-1 zeolite and 92% of alumina.

The support S1 had a specific surface area of 266 m$^2$/g.
The porosity characteristics of the matrix were:
specific surface area=233 m$^2$/g;
pore volume=0.51 cm$^3$/g;
mean mesopore diameter=8 nm.

This support S1 underwent anion exchange with hexachloroplatinic acid in the presence of hydrochloric acid as a competing agent in order to deposit 0.3% by weight of platinum with respect to the catalyst weight. The moist solid was then dried at 120° C. for 12 hours and calcined in a flow of dry air at a temperature of 500° C. for one hour.

Catalyst A obtained thereby contained, by weight, 8% of EU-1 zeolite, 91.7% of alumina and 0.3% of platinum.

EXAMPLE 3 (in Accordance)

Preparation of Catalyst B Comprising an EU-1 Zeolite

The EU-1 (1) zeolite obtained in Example 1 was then shaped by extrusion with a commercial alumina gel (Pural TH100 from Sasol) so as to obtain, after drying at a temperature of 100° C. overnight and calcining in dry air carried out at a temperature of 450° C. for 4 hours, the support S2 which contained 8% by weight of EU-1 zeolite and 92% of alumina.

The support S2 had a specific surface area of 180 m$^2$/g.
The porosity characteristics of the matrix were:
specific surface area=147 m$^2$/g;
pore volume=1.02 cm$^3$/g;
mean mesopore diameter=10 nm.

This support S2 underwent anion exchange with hexachloroplatinic acid in the presence of hydrochloric acid as a competing agent in order to deposit 0.3% by weight of platinum with respect to the catalyst weight. The moist solid was then dried at 120° C. for 12 hours and calcined in a flow of dry air at a temperature of 500° C. for one hour.

Catalyst B obtained thereby contained, by weight, 8% of EU-1 zeolite, 91.7% of alumina and 0.3% of platinum.

EXAMPLE 4

Evaluation of Catalytic Properties of Catalysts A and B in the Isomerization of Ethylbenzene The feed to be isomerized, brought into contact with catalyst A and catalyst B respectively, was solely constituted by ethylbenzene.

The isomerization operating conditions were as follows:
temperature: 400° C.;
total pressure: 9 bar (1 bar=0.1 MPa);
partial pressure of hydrogen: 7.5 bar;
feed: ethylbenzene;
hourly space velocity, expressed as kilograms of feed introduced per kilogram of catalyst per hour, equal to 8.7 h$^{-1}$.

The catalytic properties of catalysts A and B were evaluated in succession in the isomerization of ethylbenzene. Each of the catalysts was reduced in hydrogen for 4 hours at 480° C. before injecting the feed.

The catalysts were evaluated in terms of ethylbenzene conversion and selectivity for xylenes.

The selectivity for xylenes was calculated from the produced xylenes yield. The xylenes yield was determined from the percentage by weight of produced xylenes, obtained by analysis of each effluent.

The ethylbenzene conversion is the percentage of ethylbenzene consumed.

TABLE 1

Conversion of ethylbenzene and selectivity for xylenes on catalysts A and B

|  | Catalyst A | Catalyst B |
| --- | --- | --- |
| Ethylbenzene conversion (%) | 35.6% | 42.2% |
| Selectivity for xylenes (%) | 70.1 | 71.6 |
| Xylenes yield (%) | 24.95 | 30.2 |

The results presented in Table 1 show that catalyst B performed better catalytically in terms of ethylbenzene conversion than that obtained using catalyst A. Further, the selectivity for xylenes of catalyst B of the invention was improved compared with that obtained with catalyst A; as a consequence, catalyst B in accordance with the invention produced a much better xylenes yield than the xylenes yield obtained with the comparative catalyst A, the xylenes yield being the product of the ethylbenzene conversion and the selectivity for xylenes.

The invention claimed is:

1. A process for isomerizing an aromatic cut containing at least one aromatic compound containing eight carbon atoms per molecule, comprising bringing said aromatic cut into contact with at least one catalyst comprising at least one metal from group VIII of the periodic classification of the elements and at least one zeolitic support,
wherein the at least one zeolitic support comprises a zeolite selected from zeolites with structure type EUO and MOR, used alone or as a mixture, and an alumina matrix, and wherein the alumina matrix in the at least one zeolitic support of said at least one catalyst has a specific surface area in a range of 20 to less than 150 m²/g.

2. The process according to claim 1, in which the alumina matrix in the at least one zeolitic support of said at least one catalyst has a specific surface area in a range of 50 to less than 150 m²/g.

3. The process according to claim 1, in which said at least one catalyst comprises 1% to 90% by weight of zeolite with structure type EUO and/or MOR with respect to a total catalyst weight.

4. The process according to claim 1, in which the zeolite with structure type EUO is selected from the group consisting of EU-1, TPZ-3, ZSM-50,and a mixture thereof.

5. A process according to claim 4, in which the zeolite with structure type EUO is EU-1 zeolite.

6. A process according to claim 1, in which the zeolite with structure type MOR is mordenite.

7. The process according to claim 1, in which the zeolite used in the at least one zeolitic support of the at least one catalyst is a mixture of EU-1 zeolite and mordenite.

8. The process according to claim 1, in which said at least one catalyst comprises a quantity of metal(s) from group VIII in the range 0.01% to 4% by weight with respect to a total catalyst weight.

9. The process according to claim 1, in which said at least one catalyst further comprises at least one metal selected from metals from groups DIA, IVA and VIIB, said metal(s) being in a quantity of 2% by weight or less with respect to a total catalyst weight.

10. The process according to claim 1, in which the process is carried out at a temperature of 300° C. to 500° C., a partial pressure of hydrogen of 0.3 to 1.5 MPa, a total pressure of 0.45 to 1.9 MPa, and an hourly space velocity, expressed in kilograms of feed introduced per kilogram of catalyst per hour, of 0.25 to 30 h⁻¹.

* * * * *